United States Patent
Ben-Ari

(10) Patent No.: US 10,037,601 B1
(45) Date of Patent: Jul. 31, 2018

(54) SYSTEMS AND METHODS FOR AUTOMATIC DETECTION OF ARCHITECTURAL DISTORTION IN TWO DIMENSIONAL MAMMOGRAPHIC IMAGES

(71) Applicant: International Business Machines Corporation, Armonk, NY (US)

(72) Inventor: Rami Ben-Ari, Kiryat Ono (IL)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/422,483

(22) Filed: Feb. 2, 2017

(51) Int. Cl.
*G06K 9/00* (2006.01)
*G06T 7/00* (2017.01)
(Continued)

(52) U.S. Cl.
CPC .......... *G06T 7/0012* (2013.01); *A61B 6/502* (2013.01); *A61B 6/5258* (2013.01); *G06K 9/4604* (2013.01); *G06K 9/623* (2013.01); *G06K 9/6226* (2013.01); *G06K 9/6277* (2013.01); *G06K 9/6298* (2013.01); *G06K 9/66* (2013.01);
(Continued)

(58) Field of Classification Search
CPC ......... G06T 2207/30068; G06T 7/0012; G06F 19/321; A61B 6/502; G16H 50/20
USPC ............... 382/128, 171, 130; 378/37; 705/3; 707/999.006
See application file for complete search history.

(56) References Cited

U.S. PATENT DOCUMENTS 5,657,362 A * 8/1997 Giger .................... G06T 7/0012
378/37
7,616,793 B2 * 11/2009 Marshall ................ G06Q 50/24
382/128
(Continued)

FOREIGN PATENT DOCUMENTS

WO 2015017542 2/2015
WO 2015164089 10/2015

OTHER PUBLICATIONS

Sergei V. Fotin et al., "Detection of Soft Tissue Densities From Digital Breast Tomosynthesis: Comparison of Conventional and Deep Learning Approaches", Spie conference 9785-Computer aided Diagnosis, Mar. 24, 2016, pp. 105-106.
(Continued)

*Primary Examiner* — Charlotte M Baker

(57) ABSTRACT

There is provided a method, comprising: segmenting fibroglandular tissue of a 2D mammographic image of a breast, extracting regions within the segmented fibroglandular tissue and within a boundary portion between the segmented fibroglandular tissue and non-fibroglandular tissue, computing representations for each RoI by a pre-trained deep neural network, training a classifier on the representations to compute a probability score of architectural distortion for each RoI, clustering RoIs defined as positive for architectural distortion using a mean-shift method and providing an indication of the probability of the presence of architectural distortion around a cluster based on the probability distribution of cluster RoI members, removing small clusters having fewer RoI members than a small number threshold, classifying the image as positive for the indication of architectural distortion when at least one cluster remains, or classifying the image as negative for the indication of architectural distortion when no cluster remains.

20 Claims, 8 Drawing Sheets

(51) Int. Cl.
*G06T 7/11* (2017.01)
*G06K 9/46* (2006.01)
*G06K 9/66* (2006.01)
*G06K 9/62* (2006.01)
*G06T 5/00* (2006.01)
*G06T 7/136* (2017.01)
*A61B 6/00* (2006.01)
*G06N 3/08* (2006.01)

(52) U.S. Cl.
CPC .............. *G06N 3/08* (2013.01); *G06T 5/004* (2013.01); *G06T 7/11* (2017.01); *G06T 7/136* (2017.01); *G06T 2207/20081* (2013.01); *G06T 2207/30068* (2013.01); *G06T 2207/30096* (2013.01)

(56) References Cited

U.S. PATENT DOCUMENTS 9,808,217 B2 * 11/2017 Homma ............... A61B 6/5217

2010/0104154 A1 4/2010 Chan et al.
2012/0014578 A1 1/2012 Karssemeijer et al.
2016/0106388 A1 4/2016 Homma et al.
2016/0113606 A1 4/2016 Smith et al.

OTHER PUBLICATIONS

Takeshi Handa et al., "Dog-Based Detection of Architectural Distortion in Mammographic Images for Computer-Aided Detection", SICE Annual Conference (SICE), Aug. 20-23, 2012, pp. 762-767), IEEE, Akita.

Birmohan Singh et al., "Computer Aided Classification of Architectural Distortion in Mammograms Using Texture Features ", International Journal of Computer, Electrical, Automation, Control and Information Engineering; vol. 9, No. 7, 2015, pp. 1715-1720.

Hao Chen et al., "DCAN: Deep Contour-Aware Networks for Accurate Gland Segmentation", 2016 IEEE Conference on Computer Vision and Pattern Recognition, 2016, pp. 2487-2496.

* cited by examiner

| | Biswas et al. [3] | | | Inventors | | | |
|---|---|---|---|---|---|---|---|
| | Sens.(%) | Spec.(%) | Acc.(%) | Sens.(%) | Spec.(%) | Acc.(%) | AUC |
| MIAS | 84.2 | 79.1 | 81.6 | 87.8 | 80.0 | 84.1 | 0.905 |
| DDSM | 88.3 | 85.4 | 87.5 | 93.2 | 86.4 | 89.8 | 0.948 |

| | Classification | | Localization | | | Data Set | Data Source | Validation |
|---|---|---|---|---|---|---|---|---|
| | Sens. (%) | Spec. (%) | TPR | $FP_D$ | $FP_T$ | | | |
| DS-R-CNN[1] | 80.8 | 81.0 | 0.83 | 0.88 | 0.46 | 52 AD & 84 N | DDSM | Leave-One-patient-Out |
| BR x 4 | 80.8 | 57.1 | 0.88 | 1.41 | 0.91 | | | Leave-One-patient-Out |
| DS-R-CNN[2] | 80.8 | 77.4 | 0.79 | 0.95 | 0.52 | | | 5 fold patient cross valid |
| Faster R-CNN | 80.8 | 68.7 | 0.41 | 1.24 | 0.69 | | | 5 fold patient cross valid |
| Ranga[yy]an [4] | | | 0.80 | | 3.7 | 102 AD & 52 N | Proprietary | Leave-One-patient-Out |
| Matsubara [3] | | | 0.81 | | 2.6 | 168 AD & 380 N | Proprietary | |
| Yoshikawa [2] | | | 0.83 | | 1.0 | 40 AD & 160 N | DDSM | |

SYSTEMS AND METHODS FOR AUTOMATIC DETECTION OF ARCHITECTURAL DISTORTION IN TWO DIMENSIONAL MAMMOGRAPHIC IMAGES

BACKGROUND

The present invention, in some embodiments thereof, relates to automatic analysis of mammographic images and, more specifically, but not exclusively, to systems and methods for automatic detection of architectural distortion in two dimensional mammographic images.

Breast cancer is the second most common malignancy in women. While computer aided diagnosis reports a high level of sensitivity in revealing lesions and calcifications, such analysis methods typically fall short of detecting architectural distortion (AD), the third most common sign of impalpable breast cancer. Architectural distortion (AD) is an important and early sign of breast cancer that accounts for 12%-45% of breast cancer cases overlooked or misinterpreted in screening mammography.

SUMMARY

According to a first aspect, a method for using a trained statistical classifier for detecting an indication of architectural distortion in a mammographic image, comprises: receiving a two dimensional (2D) mammographic image of a breast; segmenting the fibroglandular tissue of the breast to create a segmented fibroglandular tissue region; extracting a plurality of regions within the segmented fibroglandular tissue region and within a boundary portion between the segmented fibroglandular tissue and non-fibroglandular tissue; computing representations for each RoI by a pre-trained deep neural network; training a classifier on the computed representations to compute a respective probability score of architectural distortion associated with each RoI; defining each RoI having the probability score above a threshold as positive for architectural distortion; clustering the RoIs defined as positive using a mean-shift method and provide an indication of the probability of the presence of architectural distortion around a cluster based on the probability distribution of cluster RoI members; removing small clusters created by the clustering of the RoI according to a small number threshold, wherein clusters having fewer RoI members than the small number threshold are removed; classifying the image as positive for the indication of architectural distortion when at least one cluster remains after the removing, or classify the image as negative for the indication of architectural distortion when no cluster remains after the removal; and outputting the classification of the image.

According to a second aspect, a system for using a trained statistical classifier for detecting an indication of architectural distortion in a mammographic image, comprises: a program store storing code; and a processor coupled to the program store for implementing the stored code, the code comprising: code to receive a two dimensional (2D) mammographic image of a breast; code to segment the fibroglandular tissue of the breast to create a segmented fibroglandular tissue region, extract a plurality of regions within the segmented fibroglandular tissue region and within a boundary portion between the segmented fibroglandular tissue and non-fibroglandular tissue, compute representations for each RoI by a neural network trained on a plurality of sample 2D mammographic images using automatically identified and extracted features, apply a classifier to the computed representations to compute a respective probability score of architectural distortion associated with each RoI, define each RoI having the probability score above a threshold as positive for architectural distortion, cluster the RoIs defined as positive using a mean-shift method to provide an indication of the probability of the presence of architectural distortion for each respective RoI, remove small clusters created by the clustering of the RoI according to a small number threshold, wherein clusters having fewer RoI members than the small number threshold are removed, classify the image as positive for the indication of architectural distortion when at least one cluster remains after the removing, or classify the image as negative for the indication of architectural distortion when no cluster remains after the removal; and output the classification of the image.

The systems and/or methods (e.g., code instructions stored in a storage device executed by processor(s)) provided herein provide a technical solution to the technical problem of automatically accurately identifying architectural distortion in a 2D mammographic image, for example, in terms of low rates of false negative and/or false positive detection errors. Automatic detection of architectural distortion in mammograms is a challenging technical problem due to several reasons, for example, low visual signature in particular in dense breasts, ambiguous boundaries yielding indeterminate annotation, and small available dataset. In particular, there is a lack of publicly available labeled and/or annotated images that include architectural distortion. Standard automated machine learning methods that rely on large data sets cannot be used due to the lack of available training datasets and due to difficulty in selecting representations that may accurately identify architectural distortion (i.e., with low false positive rates).

The systems and/or methods (e.g., code instructions stored in a storage device executed by processor(s)) described herein improve performance of a computing unit that performs the automatic detection. The improvement in performance may be based on an increase in accuracy of detecting the architectural distortion using existing computing resources (e.g., processor(s), and/or data storage), and/or improving the efficiency of detecting architectural distortion by a reduction in processing time, a reduction in processor utilization, and/or a reduction in data storage requirements. For example, the systems and/or methods described herein may train a classifier to perform the classification of the mammogram using high accuracy, using a relatively small size training set labeled as including architectural distortion. The classifier is trained relatively quickly due to the small size of the training set. The small sized training set requires smaller storage capacity. In another example, the trained classifier that is applied to classify a mammographic image performs the classification within a relatively short processing time, using relatively fewer processing resources, and/or using relatively smaller data storage requirements. The improvement in performance may include training the classifier and/or applying the classifier using less memory, and/or using fewer computational resources (e.g., processor(s) utilization), and/or faster computation time, without sacrificing the accuracy (and in many cases improving the accuracy) of the identifying of architectural distortion within the image.

In a first possible implementation of the method or the system according to the first or second aspects, the method and/or the system further comprise: when the image is classified as positive, applying a regression operation to the RoIs to obtain at least one localization and prediction for the RoI size indicative of the region within the 2D mammographic image where the architectural distortion is identified.

The location of the architectural distortion within the 2D mammographic image is identified.

In a second possible implementation form of the method or the system according to the first or second aspects as such or according to any of the preceding implementation forms of the first or second aspects, the method and/or system further comprise: when the image is classified as positive, applying a secondary mean-shift clustering method to the RoIs having probability scores above a second threshold, to select at least one localization RoI indicative of localization of the indication of the architectural distortion within the 2D mammographic image.

In a third possible implementation form of the method or the system according to the second implementation forms of the first or second aspects, the method and/or system further comprise: marking on the 2D mammographic image, the location of the indication of the architectural distortion corresponding to the location of the at least one localization RoI.

In a fourth possible implementation form of the method or the system according to the second or third implementation forms of the first or second aspects, the method and/or system further comprise: computing a union of a plurality of the localization RoIs, the union indicative of the indication of the architectural distortion.

In a fifth possible implementation form of the method or the system according to the first or second aspects as such or according to any of the preceding implementation forms of the first or second aspects, the fibroglandular tissue is segmented by applying an unsharp mask filter to the mammographic image to obtain a first processed image, normalizing the values of the pixels of the first processed image, and applying threshold to the normalized values to obtain the segmented fibroglandular tissue.

In a sixth possible implementation form of the method or the system according to the first or second aspects as such or according to any of the preceding implementation forms of the first or second aspects, the RoIs are extracted by sparse and random sampling of the segmented fibroglandular tissue.

The random and/or sparse sampling of the segmented fibroglandular tissue improves computations efficiency of computing unit 204, for example, by reducing processing time and/or processing resources. For example, in comparison to sampling methods that obtain samples from larger areas such as the entire breast region depicted in the image.

In a seventh possible implementation form of the method or the system according to the first or second aspects as such or according to any of the preceding implementation forms of the first or second aspects, negative RoIs are defined entirely within the segmented fibroglandular tissue.

In an eighth possible implementation form of the method or the system according to the first or second aspects as such or according to any of the preceding implementation forms of the first or second aspects, the mean shift method used for clustering the RoIs defined as positive is a non-parametric clustering technique that does not require prior knowledge of the number of clusters.

In a ninth possible implementation form of the method or the system according to the first or second aspects as such or according to any of the preceding implementation forms of the first or second aspects, the neural network is implemented as a deep neural network.

In a tenth possible implementation form of the method or the system according to the first or second aspects as such or according to any of the preceding implementation forms of the first or second aspects, the classifier is trained using deep neural network transfer learning that is based on using intermediate outputs of a pretrained neural network obtained from at least one lower layer.

In an eleventh possible implementation form of the method or the system according to the first or second aspects as such or according to any of the preceding implementation forms of the first or second aspects, the classifier is implemented as a cascade classifier implemented as a linear support vector machine (SVM).

The cascade classifier trained using the hard negatives obtains lower false-positive rates in comparison to a classifier that is not trained using hard negatives.

In a twelfth possible implementation form of the method or the system according to the first or second aspects as such or according to any of the preceding implementation forms of the first or second aspects, the method and/or system further comprise computing a symmetric overlap ratio used to validate the localization of architectural distortion, the symmetric overlap ratio denoted as:

$$\mathcal{R}_i = \mathcal{R}(p_i) = \max\left(\frac{|t \cap p_i|}{|t|}, \frac{|t \cap p_i|}{|p_i|}\right), \text{ s.t. } m \leq |p_i| \leq M$$

wherein:
t denotes an annotation set,
$p_i$ denotes the predicted RoI that includes the architectural distortion,
m, and M denote respectively the bounding lowest and highest scale factors that bound the RoI that includes the architectural distortion,
wherein the predicted mask is obtained as the union of RoIs that overlap the true mask over a certain ratio denoted as:

$$p_k = \bigcup_i \{p_i \mid \mathcal{R}_i \geq \alpha\},$$

wherein:
i denotes the index of the RoI,
k denotes the indexes of the image,
α denotes a threshold on the overlap ratio,
wherein true positive and false positive measures for localization are defined as:

$$TPR = \frac{\#\{\mathcal{R}(p_k) \geq \alpha\}}{\#\{AD \text{ findings in the images classified as true}\}}$$

According to a third aspect, a method for training a statistical classifier for detecting an indication of architectural distortion in a mammographic image of a breast, comprises: receiving a set of training 2D mammographic member images including a sub-set of 2D mammographic images labeled as positive for architectural distortion, wherein the 2D mammographic images comprise screening mammographic images, wherein the size of the sub-set being inadequate for training a standard R-CNN to achieve statistically significant classification; segmenting the fibroglandular tissue of the breast of each member image to create a segmented fibroglandular tissue region; extracting positive RoIs from regions around the identified architectural distortion of the sub-set of 2D mammographic images labeled as positive for architectural distortion; extracting negative RoIs from random regions in the fibroglandular tissues of normal mammographic images that are not labeled as positive for architectural distortion; computing representations for each RoI using a pre-trained neural network; training a binary object cascade classifier, using the computed representations, to compute a respective probability score indicative of architectural distortion associated with each RoI; and providing the trained binary object cascade classifier for classifying a new 2D mammographic image as positive for the indication of architectural distortion.

In a first possible implementation form of the method according to the third aspect, the method further comprises applying image augmentation to the positive RoIs.

In a second possible implementation form of the method according to the third aspect as such or according to any of the preceding implementation forms of the third aspect, the size of the subset is less than 100 2D mammographic images labeled as positive for architectural distortion.

In a third possible implementation form of the method according to the third aspect as such or according to any of the preceding implementation forms of the third aspect, the method further comprises training a regressor to localize the architectural distortion, based on the RoIs classified as including architectural distortion by the classifier based on a high probability score above a threshold, wherein the RoIs classified as including architectural distortion overlap an annotated region defined as including the architectural distortion.

In a fourth possible implementation form of the method according to the third aspect as such or according to any of the preceding implementation forms of the third aspect, the binary object cascade classifier is trained by returning samples incorrectly rejected at a first cascade level as input into a following cascade level.

The cascade classifier trained using the hard negatives obtains lower false-positive rates in comparison to a classifier that is not trained using hard negatives.

In a fifth possible implementation form of the method according to the third aspect as such or according to any of the preceding implementation forms of the third aspect, the training images labeled as positive for architectural distortion are annotated with a simple marking such as bounding box, defining a boundary of an annotated region containing the architectural distortion.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 7 is a table depicting performance of the RoI classification performance of the systems and/or methods described herein based on the deep neural network transfer learning in accordance with some embodiments of the present invention.

DETAILED DESCRIPTION

Figure 1:
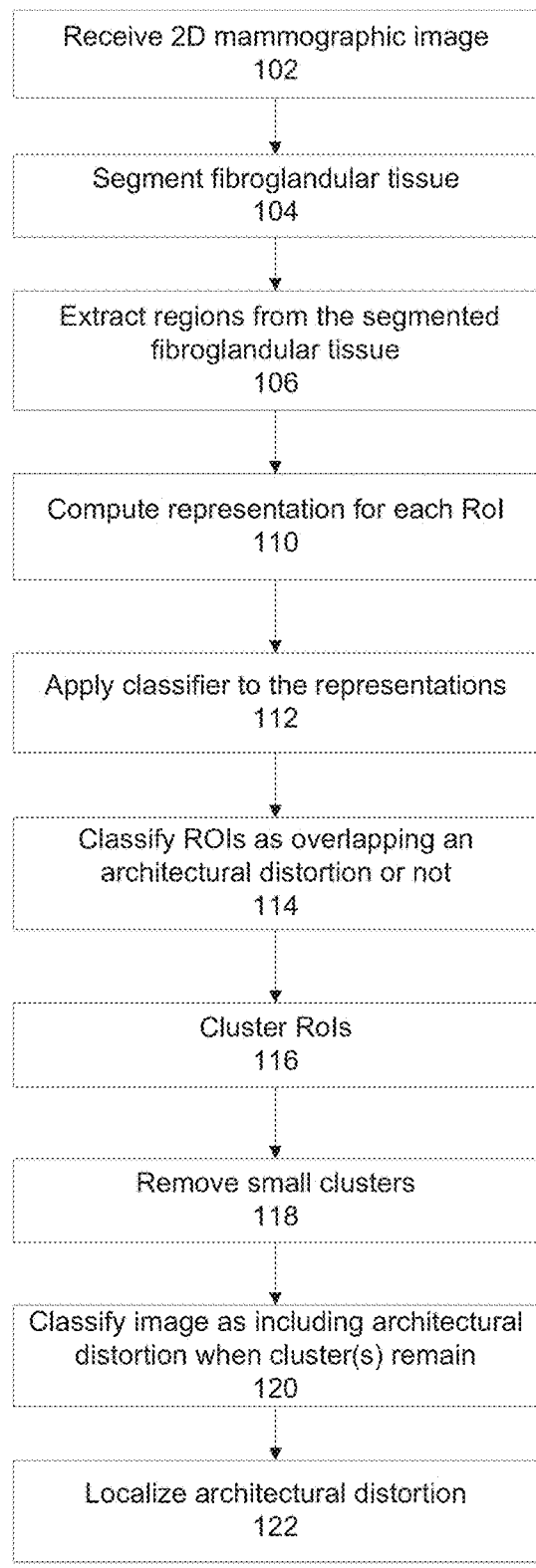
FIG. 1 is a flowchart of a method for applying a trained neural network for representation of regions of interest (RoI) from a 2D mammographic image, and/or using a trained classifier to identify the existence of architectural distortion finding in the 2D mammographic image, in accordance with some embodiments of the present invention.

The present invention, in some embodiments thereof, relates to automatic analysis of mammographic images and, more specifically, but not exclusively, to systems and methods for automatic detection of architectural distortion in two dimensional mammographic images.

An aspect of some embodiments of the present invention relates to systems and/or methods (e.g., code instructions stored in a storage device executed by one or more processors) that automatically detect an indication of architectural distortion in a two dimensional (2D) mammographic image, optionally a standard mammographic images, which may be digitally captured and/or converted into digital form for analysis. The image is processed to segment the fibroglandular tissue of the breast. The segmented fibroglandular tissue includes a boundary with the non-fibroglandular tissue. Multiple RoI (regions of interest) are identified within the segmented fibroglandular tissue, optionally by randomly and/or sparsely sampling within the segmented fibroglandular tissue. Multiple RoIs at different scales are defined for each RoI. Each RoI is encoded by a neural network, optionally a deep neural network (DNN), that is trained on a training set of 2D mammographic images using automatically computed representations of the RoI. The representations are optionally obtained through transfer learning. The representations may be computed by using intermediate outputs of the neural network. A classifier, optionally a cascade classifier, optionally a linear support vector machine (SVM), is applied to each encoded RoI to compute a probability score of the presence of architectural distortion within the region of the mammographic image defined by the RoI. RoIs scoring above a requirement (e.g., threshold) may be selected and defined as positive for being indicative for architectural distortion. Regions having associated RoIs defined as indicative for architectural distortion are clustered, optionally using a mean-shift based method. Small clusters (according to a number requirement, e.g., threshold) are removed. When no clusters remain, the 2D mammographic image is classified as negative for architectural distortion. When one or more clusters remain, the 2D mammographic image is classified as positive for architectural distortion.

Each RoI may be represented by one (or more) points (i.e., pixels) within the RoI, optionally the central point. RoI central points are then clustered in a pre-defined feature space (e.g., distance) to represent possible architectural distortion findings in certain areas. Each cluster entity is associated with a probability/score according to the probability distribution of its member RoIs (e.g., mean).

Optionally, the architectural distortion is localized within the 2D mammographic image when the image is classified as positive for architectural distortion. When multiple RoIs are identified, a regression operation may be applied to the multiple RoIs to obtain a localization and prediction for the RoI size and location indicating the region within the 2D mammographic image where the architectural distortion is identified.

Optionally, the 2D mammographic image is a screening mammogram, for example, captured using a radiation dose defined for screening mammograms. The neural network and/or classifier may be trained using 2D screening mammographic images.

An aspect of some embodiments of the present invention relates to systems and/or methods (e.g., code instructions stored in a storage device executed by one or more processors) that train a classifier to output a probability score indicative of architectural distortion within the RoI when the computed representations (extracted by a pre-trained neural network) are provided as input into the classifier. The classifier is trained to achieve accurate identification of architectural distortion using a small set of mammographic training images, where the number of images is insufficient to train a standard R-CNN.

Optionally, the size of the set of training images classified as including architectural distortion is below 100, or below 70, or below 50, or other values.

The systems and/or methods (e.g., code instructions stored in a storage device executed by processor(s)) provided herein provide a technical solution to the technical problem of automatically accurately identifying architectural distortion in a 2D mammographic image, for example, in terms of low rates of false negative and/or false positive detection errors. Automatic detection of architectural distortion in mammograms is a challenging technical problem due to several reasons, for example, low visual signature in particular in dense breasts, ambiguous boundaries yielding indeterminate annotation, and small available dataset. In particular, there is a lack of publicly available labeled and/or annotated images that include architectural distortion. Standard automated machine learning methods that rely on large data sets cannot be used due to the lack of available training datasets and due to difficulty in selecting representations that may accurately identify architectural distortion (i.e., with low false positive rates).

The systems and/or methods (e.g., code instructions stored in a storage device executed by processor(s)) described herein improve performance of a computing unit that performs the automatic detection. The improvement in performance may be based on an increase in accuracy of detecting the architectural distortion using existing computing resources (e.g., processor(s), and/or data storage), and/or improving the efficiency of detecting architectural distortion by a reduction in processing time, a reduction in processor utilization, and/or a reduction in data storage requirements. For example, the systems and/or methods described herein may train a classifier to perform the classification of the mammogram using high accuracy, using a relatively small size training set labeled as including architectural distortion. The classifier is trained relatively quickly due to the small size of the training set. The small sized training set requires smaller storage capacity. In another example, the trained classifier that is applied to classify a mammographic image performs the classification within a relatively short processing time, using relatively fewer processing resources, and/or using relatively smaller data storage requirements. The improvement in performance may include training the classifier and/or applying the classifier using less memory, and/or using fewer computational resources (e.g., processor(s) utilization), and/or faster computation time, without sacrificing the accuracy (and in many cases improving the accuracy) of the identifying of architectural distortion within the image.

In another example, the systems and/or methods described herein may train a neural network to automatically compute representations of the RoI (optionally pre-trained deep neural network) used to perform the classification of the mammogram with high accuracy, using a relatively small size training set labeled as including architectural distortion. The neural network is trained relatively quickly due to the small size of the training set. The small sized training set requires smaller storage capacity. In another example, the trained neural network that is applied to compute representations of the RoI from the mammographic image performs the automatic computation of the representation within a relatively short processing time, using relatively fewer processing resources, and/or using relatively smaller data storage requirements. The improvement in performance may include training the neural network and/or applying the neural network using less memory, and/or using fewer computational resources (e.g., processor(s) utilization), and/or faster computation time, without sacrificing the accuracy (and in many cases improving the accuracy) of the identifying of architectural distortion within the image.

In yet another example, the training of the classifier and/or neural network on the segmented fibroglandular tissue, and/or application of the classifier and/or neural network to the segmented fibroglandular tissue, results in more specific classifier and/or neural network with improved discrimination power between architectural distortion and no architectural distortion.

In yet another example, sparsely and/or randomly sampling the segmented fibroglandular tissue reduces computation time and/or processing resources, for example, in comparison to sampling larger regions of the breast image that include non-fibroglandular tissue, and/or denser sampling methods.

The systems and/or methods (e.g., code instructions stored in a storage device executed by processor(s)) described herein improve an underling technical process within the technical field of medical image processing, in particular, within the field of automatic analysis of 2D mammographic images to identify indications of breast cancer.

The systems and/or methods described herein provide a unique, particular, and advanced technique of analyzing 2D mammographic images, by applying a trained neural network and/or a trained classifier, to identify the presence of architectural distortion within the mammographic image. The systems and/or methods described herein provide a unique, particular, and advanced technique of creating a trained neural network and/or a trained classifier used to identify the presence of architectural distortion within the mammographic image.

The systems and/or methods (e.g., code instructions stored in a storage device executed by processor(s)) described herein generate new data in the form of the first classifier that automatically computes representations of the RoI from the mammographic images, and the second classifier that identifies architectural distortion in the mammographic image based on the computed representations.

The systems and/or methods (e.g., code instructions executed by one or more processors) described herein are tied to physical real-life components, for example, x-ray machines that generate the mammographic image, and computational hardware (e.g., processors, physical memory devices) that analyze the mammographic image.

Accordingly, the systems and/or methods (e.g., code instructions executed by one or more processors) described herein are inextricably tied to computer technology and/or physical components (e.g., mammogram machine, processor(s), storage device(s)) to overcome an actual technical problem arising in processing and/or analysis of 2D mammographic images.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing.

A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Accurate automatic detection of highly subtle spiculations radiating out from a center that represent the major hallmark of architectural distortion is a difficult technical problem, in particular in dense breast tissue. The systems and/or methods (e.g., code instructions stored in a storage device executed by processor(s)) described herein automatically compute representations of RoI from 2D mammographic images that are fed as input into a statistical classifier that identifies architectural distortion, which is in contrast to other methods, for example, that rely on hand-crafted features which are time consuming, difficult to design, and error prone.

The systems and/or methods (e.g., code instructions stored in a storage device executed by processor(s)) described herein accurately identify architectural distortion within a false positive and/or false negative rate that is clinically significant. Other methods that report high false positive and/or false negative detection rates are impractical for clinical use. High false positive rate may subject the patient to additional unnecessary procedures, such as invasive biopsies. High false negative rates may miss early cancer detection.

The systems and/or methods (e.g., code instructions stored in a storage device executed by processor(s)) described herein train neural networks and/or classifiers to accurately identify architectural distortion in a mammographic image using a relatively small set of training images labeled as including architectural distortion, for example, less than about 30, or 50, or 100 images may be used. Although annotated mammographic images are available in databases, such images tend to focus on tumors and/or other signs of cancer. The number of available mammographic images annotated as including architectural distortion is low.

Figure 2:
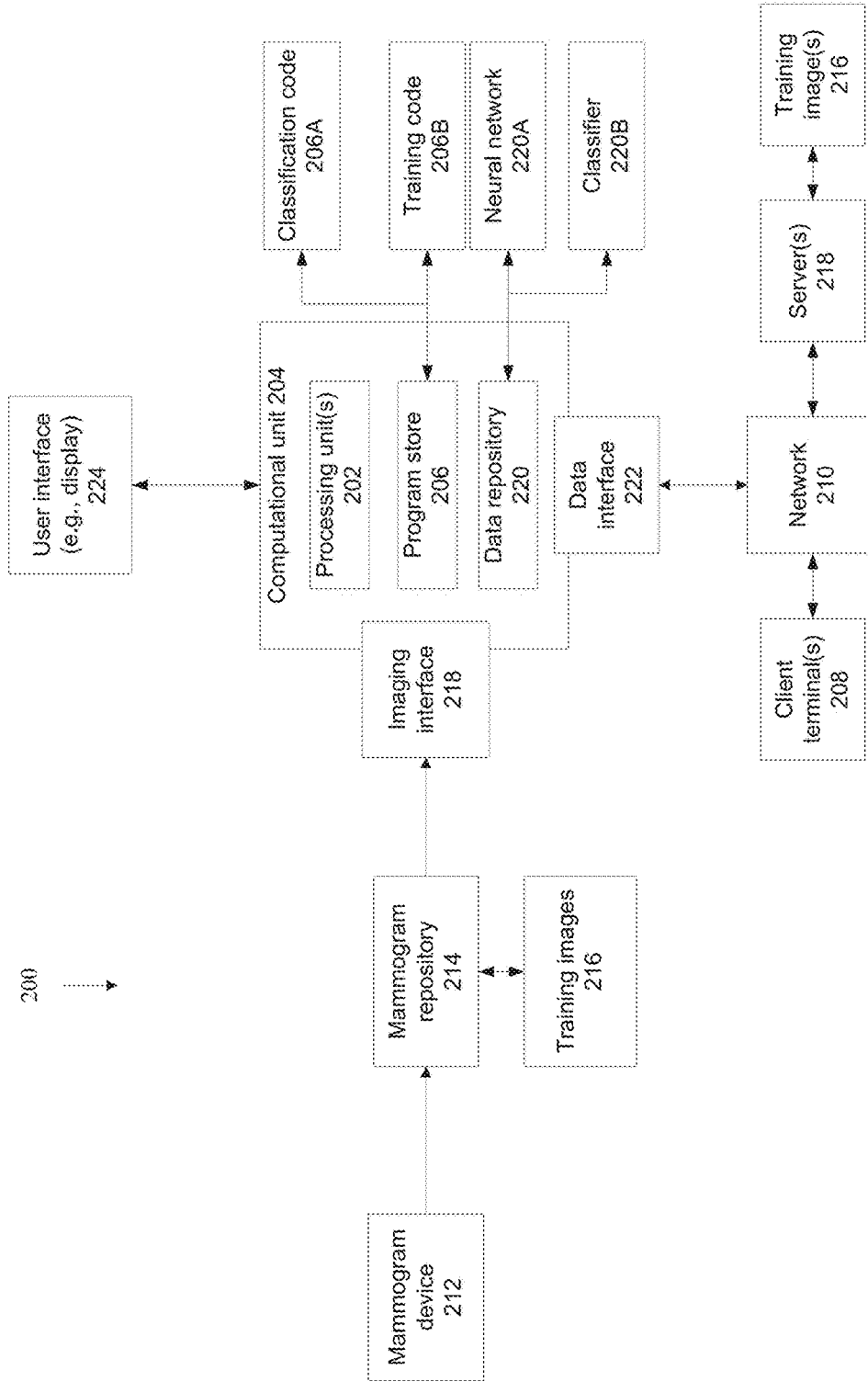
FIG. 2 is a block diagram of components of a system that applies the trained neural network to compute a representation used by a trained classifier to identify the indication of architectural distortion in the 2D mammographic image, in accordance with some embodiments of the present invention.

Reference is now made to FIG. 1, which is a flowchart of a method for applying a trained neural network to compute representations of the RoI from a 2D mammographic image, and/or using a trained classifier to use the computed representations to identify an indication of architectural distortion in the 2D mammographic image, in accordance with some embodiments of the present invention. Reference is also made to FIG. 2, which is a block diagram of components of a system 200 that applies the trained neural network to compute representations of the RoI used by a trained classifier to identify the indication of architectural distortion in the 2D mammographic image, in accordance with some embodiments of the present invention. System 200 may implement the acts of the method described with reference to FIG. 1, optionally by a processing unit 202 of a computing unit 204 executing code instructions stored in a program store 206. A method of training the neural network and/or training the classifier is described with reference to FIG. 3. The system of 200 may be used to train the neural network and/or train the classifier.

Computing unit 204 may be implemented as, for example, a client terminal, a server, a radiology workstation, a computing cloud, a mobile device, a desktop computer, a thin client, a Smartphone, a Tablet computer, a laptop computer, a wearable computer, glasses computer, and a watch computer. Computing unit 204 may include locally stored software that performed one or more of the acts described with reference to FIG. 1 and/or FIG. 3, and/or may act as one or more servers (e.g., network server, web server, a computing cloud) that provides services (e.g., one or more of the acts described with reference to FIG. 1 and/or FIG. 3) to one or more client terminals 208 (e.g., remotely located radiology workstations) over a network 210, for example, providing software as a service (SaaS) to the client terminal(s) 208, providing an application for local download to the client terminal(s) 208, and/or providing functions using a remote access session to the client terminals 208, such as through a web browser.

Computing unit 204 receives 2D mammographic image(s) captured by a mammogram machine(s) 212, for example, a standard 2D mammographic imaging device Mammographic images captured by mammogram machine 212 may be stored in a mammogram repository 214, for example, a storage server, a computing cloud, and a hard disk. The mammographic images stored by mammogram repository 214 may include mammogram images of patients for analysis, and/or training images 216 that have been previously analyzed (e.g., by radiologists) and labeled with findings indicative of architectural distortion. Training images 216 are used to train the neural network and/or classifier, as described herein. It is noted that training images 216 may be stored by a server 218, accessibly by computing unit 204 over network 210, for example, a publicly available training dataset available from MIAS (Mammogram Image Analysis Society) and/or DDSM (Digital Database for Screening Mammograms).

Computing unit 204 may receive the mammographic image(s) using one or more imaging interfaces 218, for example, a wire connection (e.g., physical port), a wireless connection (e.g., antenna), a network interface card, other physical interface implementations, and/or virtual interfaces (e.g., software interface, application programming interface (API), software development kit (SDK)).

Program store 206 stores code instructions implementable by processing unit 202, for example, a random access memory (RAM), read-only memory (ROM), and/or a storage device, for example, non-volatile memory, magnetic media, semiconductor memory devices, hard drive, removable storage, and optical media (e.g., DVD, CD-ROM). For example, program store 206 may store classification code instructions 206A that execute one or more acts of the method described with reference to FIG. 1, and/or training code instructions 206B that execute one or more acts of the method described with reference to FIG. 3.

Computing unit 204 may include a data repository 220 for storing data, for example, a trained neural network 220A for computing representations of the RoI from 2D mammographic images (as described herein), and/or a trained classifier 220B for identifying architectural distortions based on the representations (as described herein). Data repository 220 may be implemented as, for example, a memory, a local hard-drive, a removable storage unit, an optical disk, a storage device, and/or as a remote server 218 and/or computing cloud (e.g., accessed over network 210). It is noted that neural network 220A and/or classifier 220B may be stored in data repository 220, for example, with executing portions loaded into program store 206 for execution by processing unit 202.

Computing unit 204 may include data interface 222, optionally a network interface, for connecting to network 210, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing unit 204 may access one or more remote servers 218 using network 210, for example, to download updated training images 216.

Computing unit 204 may connect using network 210 (or another communication channel, such as through a direct link (e.g., cable, wireless) and/or indirect link (e.g., via an intermediary computing unit such as a server, and/or via a storage device) with one or more of:
- Client terminal(s) 208, for example, when computing unit 204 acts as a server providing SaaS to remote radiology terminals, by analyzing remotely obtained mammographic images for the presence of architectural distortion.
- Server 218, for example, when server 218 is part of picture archiving and communication system (PACS), which may storage large numbers of mammographic images for analysis, for example, captured by a mammographic machine of a radiology clinic.
- Mammogram repository 214 that stores mammographic images.

Computing unit 204 includes or is in communication with a user interface 224 allowing a user to enter data and/or view the classification result and/or view the mammographic image. Exemplary user interfaces 224 include, for example, one or more of, a touchscreen, a display, a keyboard, a mouse, and voice activated software using speakers and microphone.

Referring now to FIG. 1, at 102, a two dimensional (2D) mammographic image of a breast is received by computing unit 204. The 2D mammographic image may be obtained by mammogram machine 212, for example, as part of a routine breast cancer screening mammogram. The 2D mammographic image may be stored in mammogram repository 214 (e.g., a hard drive of mammogram machine 212, a PACS server, a CD-ROM disk provided to the patient) and provided to computing unit 204 using imaging interface 218 (e.g., network connection, CD-ROM drive, cable connection).

At 104, the fibroglandular tissue of the breast is automatically segmented to create a segmented fibroglandular tissue region. The segmented fibroglandular tissue region includes a boundary portion between the identified fibroglandular tissue and non-fibroglandular tissue.

The mammographic image may be processed to detect the pectoral muscle, which may be masked out as an irrelevant region.

The mammographic image may be processed to detect the outline of the breast, which may be used to guide the segmentation process.

The fibroglandular tissue may be segmented by applying an unsharp mask filter to the 2D mammographic image. The resulting processed image may be normalized, optionally by normalizing the values of the pixels of the resulting processed image to the range [0,1].

The segmented fibroglandular tissue may be obtained by setting a threshold over $I_{hpf}$, and optionally applying post-processing.

$$I_{hpf}=\alpha I-G*I, \quad \text{[equation 1]}$$

where:
- $\alpha$ denotes a constant factor,
- G denotes a Gaussian,
- * denotes standard convolution,
- I denotes the provided 2D mammographic image.

At 106, regions of interest are extracted from the segmented fibroglandular tissue region. The regions may be defined as points within the segmented fibroglandular tissue, a set of coordinates within the segmented fibroglandular tissue, and/or pixels within the segmented fibroglandular tissue.

The RoIs may be identified based on a random sampling within the interior of the segmented fibroglandular tissue, and/or the boundary regions of the segmented fibroglandular tissue.

Optionally, the RoIs are obtained based on a sparse sampling. Sparse sampling is performed by sampling less than a predefined percentage of the pixels in the segmented fibroglandular tissue, for example, less than about 5%, or 2%, or 1%, or 0.6%, or 0.5%, or 0.2%, or other smaller, intermediate, or larger percentages. The percentage of the pixels for sampling may be dynamically set according to the size of the fibroglandular region segmented from the image.

Sparse sampling may be performed using the following described exemplary method: preset the number of points (i.e. pixels) to be sampled from the interior of the segmented fibroglandular tissue region and separately from the boundaries of the segmented fibroglandular tissue region. The sampled points (i.e., pixels) in the fibroglandular tissue region are represented as a vector in a random order. The points are sampled from the vector by a constant stride according to the preset number of sampled points. The process is performed for the segmented fibroglandular interior points and again for the segmented fibroglandular boundary. The points (corresponding to RoIs) are collected for DNN encoding and classification, as described herein. It is noted that at each point several RoIs at different scales (size of the bounding box) are extracted.

The random and/or sparse sampling of the segmented fibroglandular tissue improves computations efficiency of computing unit 204, for example, by reducing processing time and/or processing resources. For example, in comparison to sampling methods that obtain samples from larger areas such as the entire breast region depicted in the image.

The sparse sampling may be justified by the shift invariant property of neural network (e.g., CNN) representation (e.g., gained in the clustering phase) and/or the shift image augmentation performed in the training set.

Figure 4:
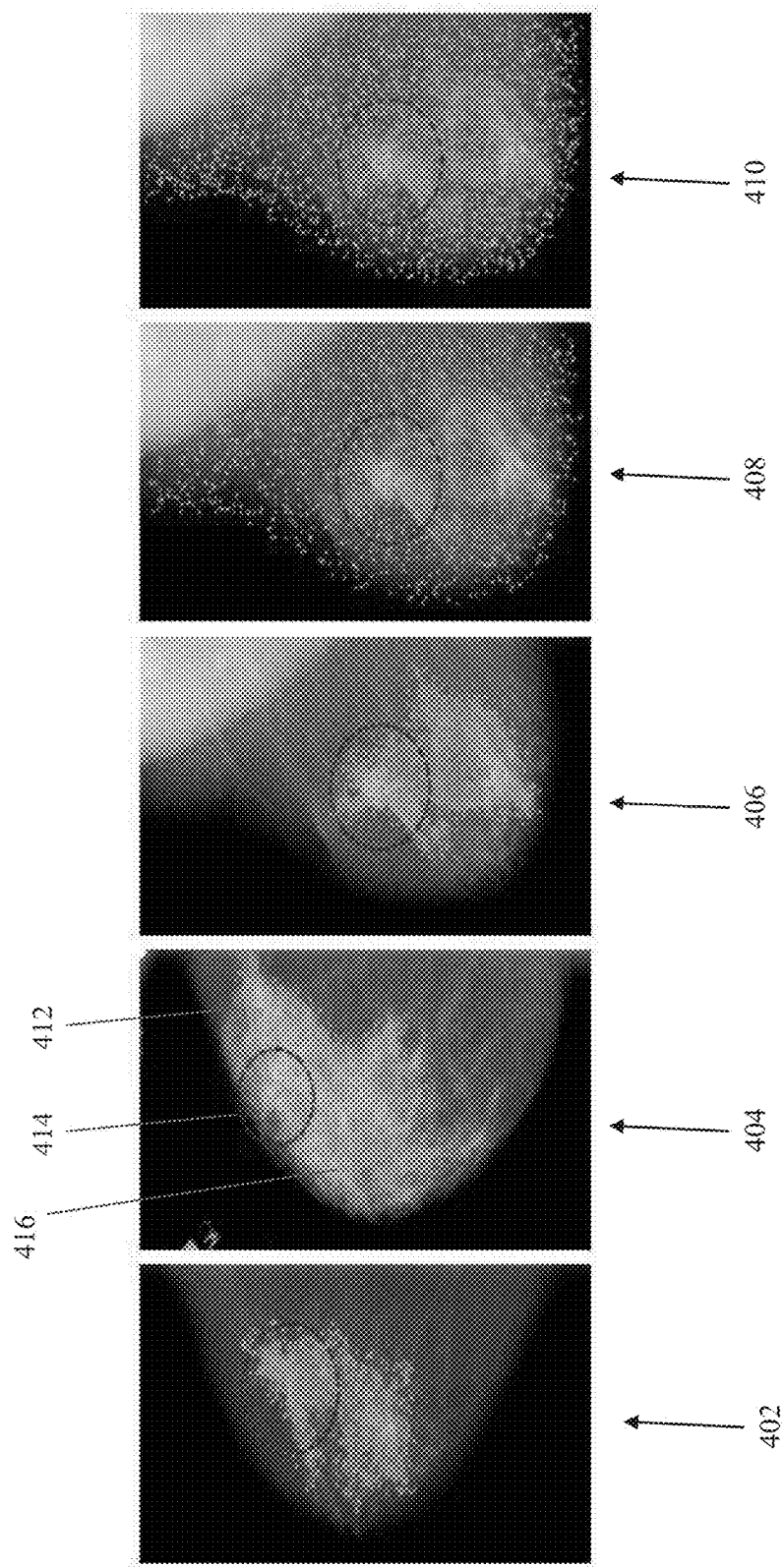
FIG. 4 includes 2D mammographic images depicting a comparison of random sampling of the segmented fibroglandular tissue in comparison to sampling of the whole breast, in accordance with some embodiments of the present invention.

Reference is now made to FIG. 4, which includes 2D mammographic images depicting a comparison of random sampling of the segmented fibroglandular tissue in comparison to sampling of the whole breast, in accordance with some embodiments of the present invention. The images show that to obtain a similar coverage of the architectural distortion domain, sampling from the whole breast requires (on average) about 2-4× as many samples as sampling in the segmented fibroglandular tissue segment.

Images 402, 404, and 406 depict images processed using ransom and sparse sampling methods within the segmented fibroglandular tissue. Images 408 and 410 depict image 406 processed by sampling the entire breast region. Image 408 depicts a 2× sampling rate in comparison with image 406, and image 410 depicts a 4× sampling rate in comparison with image 406.

Dots 412 (appearing in all images 402-410, but shown only in one image for clarity) represent the sampling regions. Circle 414 (appearing in all images 402-410, but shown only in one image for clarity) represents a portion of the respective image containing architectural distortion that includes a high concentration of sample points restricted to the segmented fibroglandular tissue region. Region 416 (appearing in images 402-406, but shown only in one image for clarity) denotes the segmented fibroglandular tissue region.

RoIs are defined at different scales The scale selection may be based on the dataset, such as extent of variation of the AD finding. For example, 3 different scales may be used, 1, 1.2, and 1.4 based on a nominal ROI size of 128×128 pixels (corresponding to approximately 25×25 millimeters). The RoIs may be defined using a common shape, for example, a square, a rectangle, a triangle, and a circle. The RoIs may be defined at a common place, for example, at the center of each RoI.

In terms of mathematical representation, each sample point may define a set of RoIs at different scales, represented as $r_i^k$, where k indexes the image, and i indexes the particular RoI for the certain point sample.

At 110, representation(s) (i.e., deep learning representations) are computed for each RoI. Each RoI is encoded by a neural network that automatically computes representations of the RoI from the image data defined by the RoI. The neural network maybe trained using a training set of 2D mammographic images labeled as indicative of architectural distortion or pre-trained on another dataset, for example, as described with reference to FIG. 3.

The encoded representation of each RoI may be represented as a feature vector, for example, a 128 dimension vector, or other larger or smaller dimensions may be used.

The network may be trained on publicly available data, for example, ImageNet data by the visual geometry group (VGG) of the University of Oxford.

Optionally, the neural network is a deep neural network.

Optionally, the neural network is a convolutional neural network (CNN).

Optionally, the neural network is a CNN-M, as described with reference to Chatfield, K., Simonyan, K., Vedaldi, A., Zisserman, A.: Return of the devil in the details: Delving deep into convolutional nets. In: British Machine Vision Conference (2014), incorporated herein by reference in its entirety, was used. The CNN-M network includes 5 convolution layers, three fully connected layers and a SoftMax layer with 1000 output nodes.

Optionally, a modification of the CNN-M network is used. The modification may be used when the size of the training dataset includes a small number of training images. The modified CNN-M includes, for example, low dimensional full 7 layer resulting in 128D output at 20th layer.

Optionally, each RoI image is processed to enable and/or improve the computation of the representations of the RoI. Optionally, each RoI is resized according to the input layer of the network, for example, to 224×224.

It is noted that the neural network may be fine-tuned using a significant amount of labeled images, which are generally not publicly available. The number of publicly available images that include annotated architectural distortion is limited. The training set may be enhanced using image augmentation conducted on positively labeled samples, for example, by performing random shifts, rotations and flips. For example, each image may be augmented for a total of 10 augmented samples by performing 5 random shifts, 3 rotations, and 2 flips.

At 112, a classifier is applied to the computed representations of each RoI. Optionally, the classifier is applied to the feature vector extracted for each RoI. The classifier outputs a probability score indicative of the probability of the presence of architectural distortion within the image portion defined by the respective RoI. Training of the classifier is described, for example, with reference to FIG. 3.

In terms of mathematical representation, C: $r_i^k \to s$, where C denotes the applied classifier, and s denotes the outputted probability score.

Optionally, the classifier is implemented as a cascade classifier. Optionally the cascade classifier is implemented as a linear support vector machine (SVM).

The cascade classifier is created to preserve a high detection rate while significantly reducing false-positives. When the data set is small (about 50 images labeled as positive for architectural distortion), all the positive samples may be used for training the classifier. The stage linear-SVM classifiers may be trained on balanced sets by random sampling from the large negative set. The thresholds at each level are determined according to the predefined (e.g., allowed) true-positive rate.

Optionally, the cascade classifier is trained by returning samples incorrectly rejected in a certain cascade level into the training process at the following cascade level. Training the classifier using the incorrectly rejected images improves sensitivity to false negatives, which is important to avoid missing cancer by incorrectly labeling the image as not including architectural distortion when in fact architectural distortion exists in the image. Applying the cascade classifier in the fibroglandular tissue domain rather than the whole breast creates a domain specific classifier directly trained on hard negatives. The emerged classifier may better discriminate between different patterns of fibroglandular tissues as required from the visual task.

At 114, RoIs are positively classified as overlapping an architectural distortion (i.e., including a portion or the entire architectural distortion within the RoI) or not overlapping architectural distortion (e.g., it is noted that the negative classification may include an insignificant or small portion of the architectural distortion). RoIs having probability scores according to a requirement (e.g., above a threshold) as designated as positive for being indicative of architectural distortion within the image portion defined by the respective RoI.

The threshold may be selected, for example, as 0.5, where RoIs having probability scores equal to or above 0.5 are defined as positive for architectural distortion. It is noted that setting a higher value for the threshold may significantly reduce false positives, in expense of possible false-negatives.

At 116, RoIs defined as positive are clustered. The clustering may be performed using one or more points of the RoIs, optionally the central points. The clustering may be performed using a mean-shift method, for example, as described with reference to Comaniciu, E., Meer, P.: Mean shift: A robust approach toward feature space. IEEE Trans. Pattern Anal. Machine Intell. 24, 603619 (2002), incorporated herein by reference in its entirety. The clustering provides an indication of the probability of the presence of architectural distortion for each respective region.

The mean shift method that clusters the regions may be a non-parametric clustering technique that does not require prior knowledge of the number of clusters At 118, small clusters created by the clustering of the regions are removed. The removal may be performed according to a small number requirement, for example, a threshold. Clusters having a number of members less than or equal to the threshold are removed. Exemplary thresholds include, 5, 10, 15, 20, and 25 or other values which may vary, for example, according to a target accuracy rate. Exemplary ranges for selection of the threshold include 10-20, or 5-25.

The removal of the small clusters may be based on the assumption that the small clusters are caused by sporadic false-detections. Dense clusters are suggestive of the indication of architectural distortion.

At 120, the 2D mammographic image is classified. When one or more clusters remain after the removal process, the mammographic image is classified as positive for the indication of including architectural distortion. When no clusters remain after the removal process, the mammographic image is classified as negative for the indication of inexistence of architectural distortion.

Optionally, at 122, the indication of the architectural distortion is localized in the 2D mammographic image.

The architectural distortion may be localized using a regression operation applied to multiple RoIs to obtain a localization and prediction for the RoI size indicating the region within the 2D image where the architectural distortion is identified. Alternatively, the architectural distortion may be localized by applying a secondary mean-shift clustering method to the RoIs associated with each respective region that have probability scores above a second requirement, for example, a second threshold. The second threshold may be selected to have a value greater than the first threshold, to consider the RoIs most likely to include architectural distortion.

When each region is associated with two or more RoIs likely to include architectural distortion (the RoIs overlap), a union operation may be applied to RoIs. The union operation outputs a region indicative of the location of the architectural distortion within the 2D mammographic image.

Architectural distortion may be detected in multiple sampled RoIs, and/or may be detected in a small region in a RoI. The variation in the location of the architectural distortion may be due, for example, to the large scale variability in the annotation of images (e.g., ×5 scale ratio) and/or due to unclear architectural distortion boundaries.

With respect to blocks 120 and/or 122, the classification of the mammographic image is provided. For example, the positive or negative indication for the presence of architectural distortion may be presented on a display (e.g., as a text message), stored within an electronic medical record of the patient, and/or stored as a label and/or in a field associated with the mammographic image stored by a PACS server.

When the image is identified as positive for the presence of architectural distortion, and an RoI or union is identified (based on the regression operation and/or secondary clustering method), the RoI or union may be marked on the mammogram image to define the location in which the architectural distortion is found, for example, using a box that may be color coded, an arrow pointing to the architectural distortion, a set of coordinates defining the location, or other implementation.

A radiologist may further manually investigate the defined location on the mammographic image to validate the automated findings and/or reject the automated findings.

It is noted that when a certain mammographic image is automatically classified as being positive for architectural distortion, but upon radiological review and/or other testing (e.g., biopsy) architectural distortion is not found, the certain mammographic image may represent a hard negative finding. The certain mammographic image may be labeled as being negative for architectural distortion and fed back to update the classifier.

Figure 3:
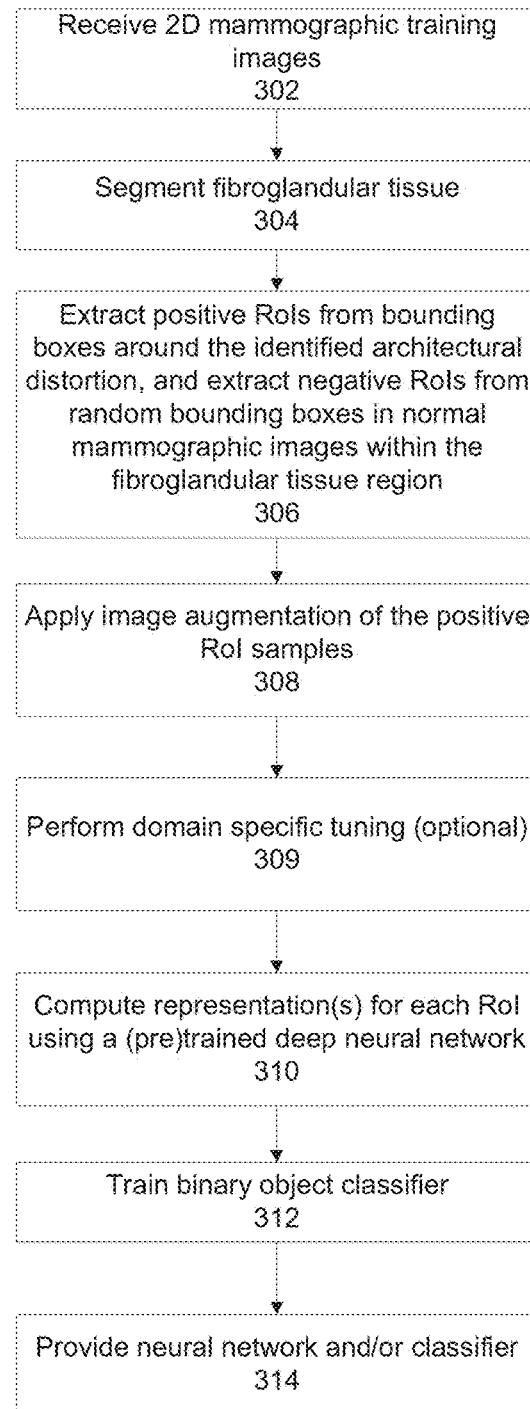
FIG. 3 is a flowchart of a method for training the classifier/network to output a probability indicative of architectural distortion, in accordance with some embodiments of the present invention.

Reference is now made to FIG. 3, which is a flowchart of a method for training the neural network to extract features from the mammographic image, and/or for training the classifier to output a probability indicative of architectural distortion, in accordance with some embodiments of the present invention. The trained neural network and/or trained classifier may be used to detect the indication of architectural distortion, as described with reference to FIG. 1. The components of system 200 described with reference to FIG. 2 may implement the method described with reference to FIG. 3, for example, computing unit 204 may execute training code 206B, to create neural network 220A and/or classifier 220B.

The method described with reference to FIG. 3 creates a novel neural network that identifies the indication of architectural distortion in a 2D mammographic images with statistically significant accuracy (at least a low false positive rate), using a relatively small set of training images.

The systems and/or methods described with reference to FIG. 3 train the classifier and/or neural network using loosely marked annotations (e.g., rectangle, circle, free hand markings) without necessarily requiring accurately delineated findings. Hand crafted features are not necessarily used.

At 302, a set of training 2D mammographic images 216 is received. The set includes a sub-set of 2D mammographic images labeled as positive for architectural distortion. Optionally, the training images classified as including architectural distortion are annotated with a marking defining a boundary containing the architectural distortion, for example, most of the distortion, at least 70%, or at least 80%, or at least 90% of the architectural distortion. The marking may be, for example, a square, a circle, and/or free-style markings that define a border.

Training images 216 may be obtained, for example, from a publicly available database that includes pre-annotated images (e.g., as described herein), and/or created by a radiologist manually marking captured images.

Optionally, the size of the sub-set is inadequate (i.e., too small) for training a standard neural network (e.g., R-CNN) to achieve statistically significant classification. For example, the size of the sub-set includes less than about 100 images labeled as positive for architectural distortion, or less than about 70 images, or less than about 50 images, or less than about 30 images.

It is noted that typical R-CNN methods use hundreds of images per class, which are difficult to obtain in many medical applications, for example, due to rarity of the prevalence of the medical condition, and/or lack of publicly available images due to privacy issues, risk of medical malpractice, and/or manual labor required to annotate the images. An example of a typical R-CNN is described, for example, with reference to Girshick, R., Donahue, J., Darrell, T., Malik, J.: Rich feature hierarchies for accurate object detection and semantic segmentation. CVPR (2014), incorporated herein by reference in its entirety.

Training images 216 including known architectural distortion may be tagged, for example, using metadata, as indicative of architectural distortion, positive, or another classification representing architectural distortion. Training images 216 without architectural distortion (e.g., normal images) may be tagged as normal, negative, no architectural distortion, or other classification representing lack of architectural distortion.

Optionally, the training images include 2D screening mammogram images.

At 304, the fibroglandular tissue of the breast of each mammographic images is segmented to create a segmented fibroglandular tissue region, for example, as described with reference to block 104 of FIG. 1.

At 306, positive RoIs (indicative of inclusion of architectural distortion) are extracted from regions (e.g., boxes) around the identified architectural distortion of each mammographic image known to include architectural distortion, for example, as described with reference to block 106 of FIG. 1. Negative RoIs (indicative of lack of inclusion of architectural distortion) are extracted from normal mammographic images, optionally from bounding regions (e.g., boxes) within the fibroglandular tissues. The bounding boxes may be randomly selected using random sampling methods.

A set of RoIs, optionally at different scales, are defined, for example, as described herein.

Optionally, the RoIs are defined entirely within the segmented fibroglandular tissue. Alternatively, the RoIs are defined mostly within the segmented fibroglandular tissue, for example, at least 70%, or 80%, or 90%, or other values.

The set of positive and negative RoIs are used to train a domain specific classifier that more accurately discriminates between tissues including architectural distortion and tissues not including architectural distortion.

At 308, image augmentation is applied to the positive RoI samples. For example, one or more random shifts, rotations, and/or flips.

At 309, optionally domain specific fine tuning is performed.

At 310, a pre-trained neural network(s) may be used to compute representation(s) for each RoI. Each RoI may be encoded. The neural network is described, for example, with reference to block 110 of FIG. 1. Additional details are described herein.

The pre-training of the neural network may be conducted on natural images or similar medical data sets. The neural network is used to create a rich representation of mammographic RoIs. The binary object cascade classifier is trained to output a probability indicative of architectural distortion in a RoI based on the DNN.

Optionally, the R-CNN implementation of the neural network is based on Caffe implementation and/or VGG-16 architecture, for example, as described with reference to Chatfield, K., Simonyan, K., Vedaldi, A., Zisserman, A.: Return of the devil in the details: Delving deep into convolutional nets. In: British Machine Vision Conference (2014), incorporated herein by reference in its entirety.

Optionally, in a first stage termed Region Proposal Network (RPN), described with reference to Ren, S., He, K., Girshick, R., Sun, J.: Faster R-CNN: Towards real-time object detection with region proposal networks. In: NIPS (2015) (incorporated herein by reference in its entirety), a deep fully convoluted network that generates RoI candidates (also referred to as object proposals) is created.

Optionally, the neural network is implemented as a domain specific R-CNN (DS-RCNN).

At 312, a classifier (optionally a binary object classifier, optionally a cascade classifier, optionally a SVM classifier) is trained, using the encoded RoIs as inputted extracted features, and/or using the classification type of the image (e.g., positive for architectural distortion, negative for architectural distortion). The cascade classifier is trained to compute a probability score indicative of architectural distortion associated for a given RoI provided as input. The classifier is described, for example, with reference to block 112 of FIG. 1. Additional details are described herein.

Optionally, the classifier is trained by using representations computed from at least one lower layer of the neural network.

Optionally, the classifier (optionally a cascade linear SVM) is trained using negative samples obtained from random RoIs extracted from the segmented fibroglandular tissue region of mammographic images classified (e.g., tagged) as normal (or negative, or other classification indicative of lack of architectural distortion). The negative samples represent healthy tissue and/or tissue without architectural distortion.

Optionally, at each cascade level, the cascade classifier is trained using the mammographic images classified as indicative of architectural distortion (e.g., positive images), optionally the classifier is trained using all positive images. The classifier may be trained using a balancing set of images classified as negative for architectural distortion, obtained by a random sample of the false positive classification of the previous stage (sometimes referred to as hard negatives). Image that actually include architectural distortion, but are incorrectly classified by one or more of the cascade training stages as not including architectural distortion are defined as positive for architectural distortion (e.g., manually by a user) and fed as input into the next cascade level. The cascade classifier trained using the hard negatives obtains lower false-positive rates in comparison to a classifier that is not trained using hard negatives.

Optionally, a regressor (and/or another classifier implementation) is trained based on the RoIs classified as including architectural distortion by the classifier (e.g., according to a threshold applied to the probability outputted by the classifier) that overlap the annotated region defined as including the architectural distortion.

At 314, the trained neural network and/or the trained classifier are provided for classifying a new 2D mammographic image as positive for the indication of architectural distortion, and/or as negative for architectural distortion. The trained neural network and/or classifier may be locally stored, for example, by a server providing services to remote client terminals that upload mammographic images and receive the classification output. The trained neural network and/or classifier may be transmitted to remote servers, for example, to provide local analysis for 2D mammographic images, for example, to radiology clinics.

Figure 5:
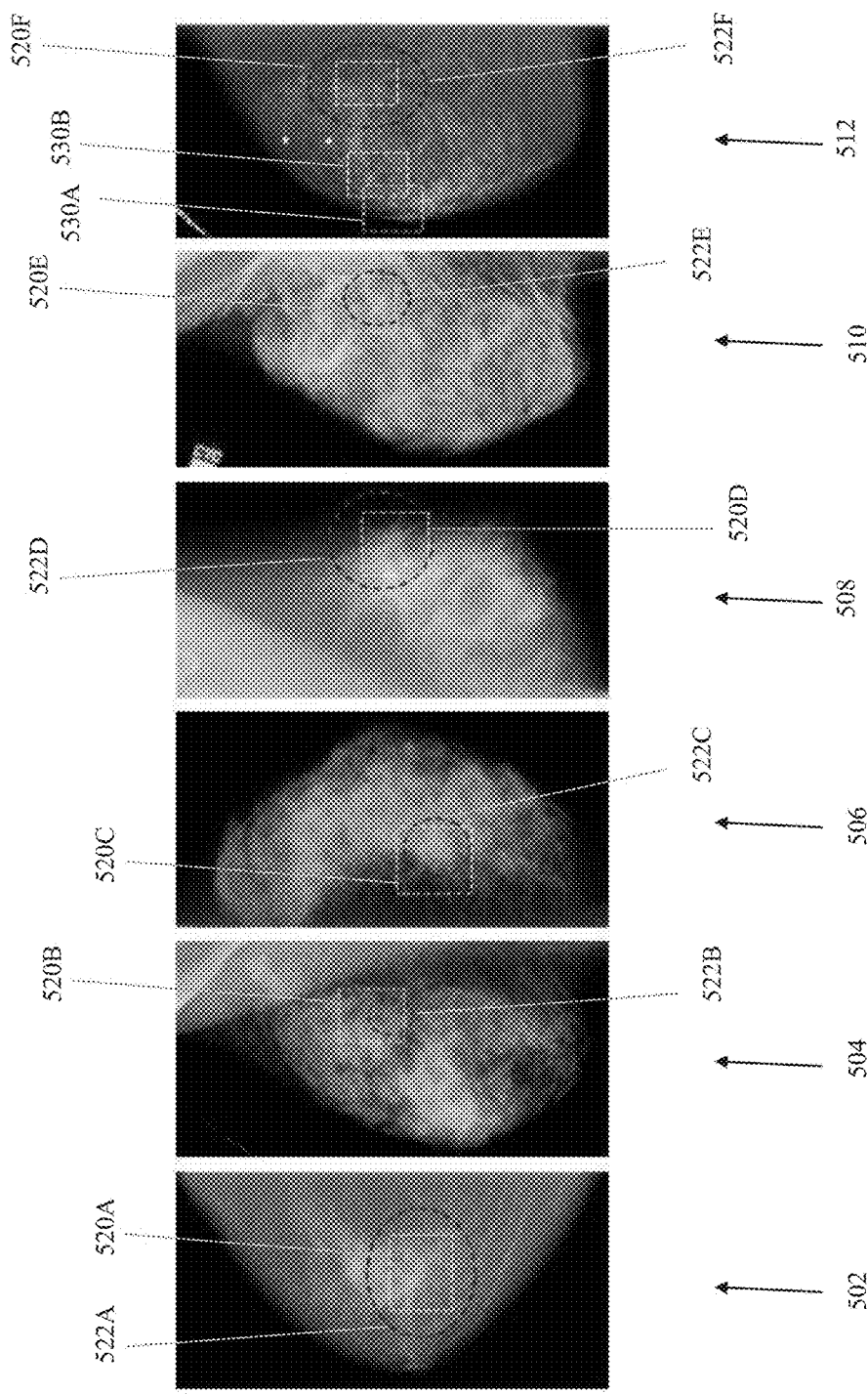
FIG. 5 is a set of mammographic images depicting localization results of architectural distortion, in accordance with some embodiments of the present invention.

Reference is now made to FIG. 5, which is a set of mammographic images depicting localization results of architectural distortion, in accordance with some embodiments of the present invention. Localization of architectural distortion is accurately performed in cases of dense breasts (the prevalence of the fibroglandular tissue in the breast), which may obscure the architectural distortion.

Each image 502, 504, 506, 508, 510, and 512 depicts a region (shown as a respective square 520A-F) localizing the detected architectural distortion. For comparison purposes, a manually annotated region (shown as a respective circle 522A-F) is depicted. The manually annotated region denotes a finding by a radiologist. The placement of the manually annotated region and the automatic identification of the architectural distortion region in a set of test images is described below with reference to the computational evaluation performed by the inventors.

Image 512 depicts a case with two false positive detections 530A and 530B. False positive detection is described below with reference to the calculated evaluation performed by the inventors.

Figure 6:
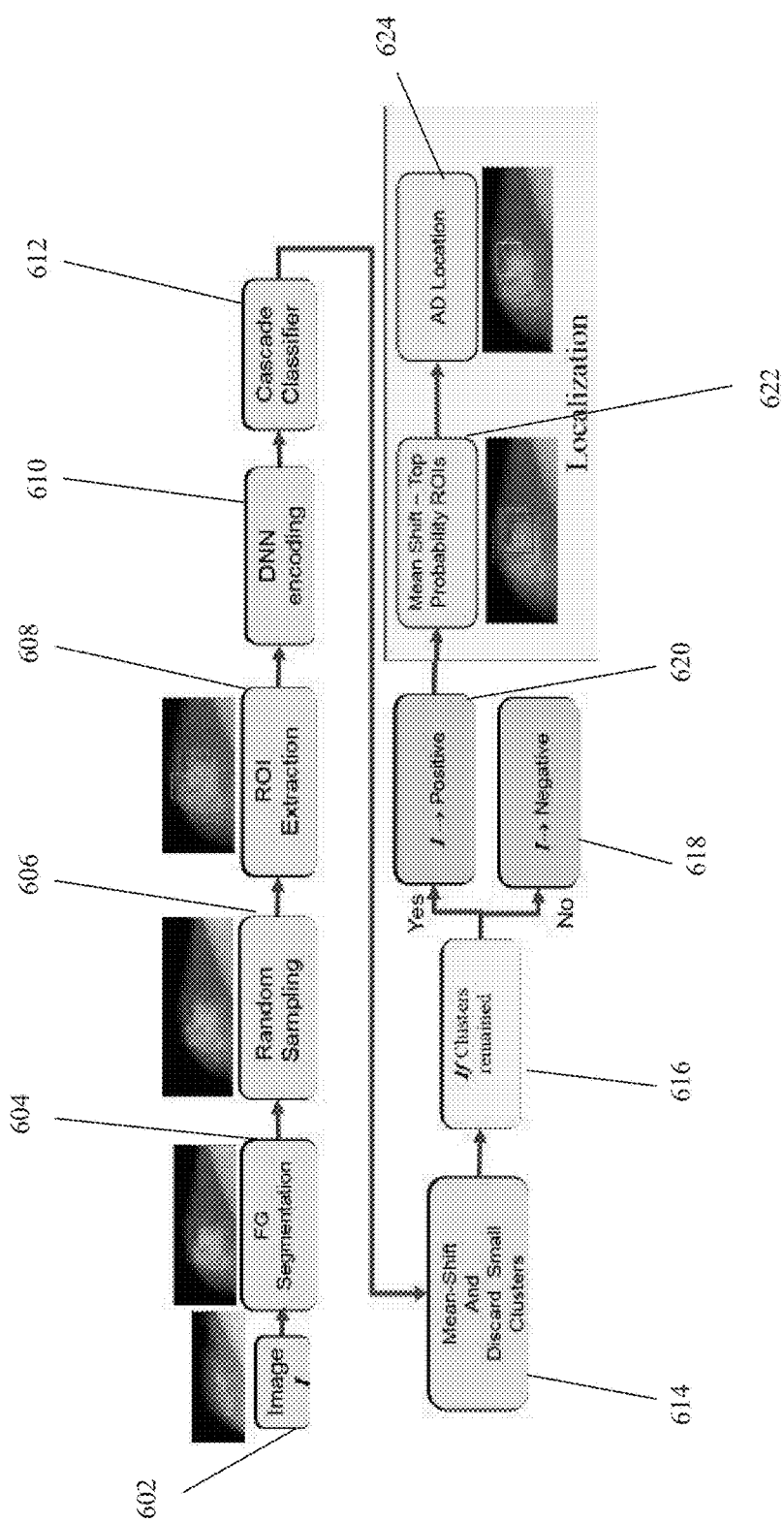
FIG. 6 is another flowchart of an exemplary method for identifying architectural distortion in a mammographic image, in accordance with some embodiments of the present invention.

Reference is now made to FIG. 6, which is another flowchart of an exemplary method for identifying architectural distortion in a mammographic image, in accordance with some embodiments of the present invention. The method described with reference to FIG. 6 may be a variation of the method describe with reference to FIG. 1. One or more acts of the method described with reference to FIG. 6 may be executed by components of system 200 described with reference to FIG. 2.

At 602, a mammographic image is received, for example, as described herein.

At 604, a fibroglandular tissue region is segmented from the mammographic image, for example, as described herein.

At 606, the segmented fibroglandular tissue region is randomly sampled, for example, as described herein.

At 608, one or more RoIs are extracted at each sample point, for example, as described herein.

At 610, each RoI is encoded using a DNN, for example, as described herein.

At 612, the computed representations of the RoI are processed by a cascade classifier, optionally a linear SVM, for example, as described herein.

At 614, a mean-shift process is applied to the output of the cascade classifier. Small clusters are discarded.

At 616, the remaining clusters are evaluated.

At 618, when no clusters remain, the image is classified as negative for being indicative of architectural distortion.

At 620, when one or more clusters remain, the image is classified as positive for being indicative of architectural distortion.

At 622, a localization process is performed by applying a regression operation and/or a secondary mean-shift process to the RoIs with the highest probability of including architectural distortion (e.g., according to a threshold).

At 624, the architectural distortion is localized within the image. The location may be marked on the image, for example, with a square having a distinct color.

Various embodiments and aspects of the present invention as delineated hereinabove and as claimed in the claims section below find calculated support in the following examples.

EXAMPLES

Reference is now made to the following examples, which together with the above descriptions illustrate some embodiments of the invention in a non limiting fashion.

Inventors performed a computational evaluation according to the systems and/or methods (code instructions stored in a storage device executed by one or more processors) described herein, for example, with reference to FIGS. 1-3, to evaluate classification of a mammographic image as including architectural distortion or as not including architectural distortion. As below in additional detail, the systems and/or methods described herein significantly reduced the error rate of architectural distortion detection in comparison with other published detection methods. The systems and/or methods described herein detected architectural distortion findings using a neural network and/or classifier trained using as little as 52 positive images (annotated as including architectural distortion) obtained from 42 patients. The systems and/or methods are computationally efficient, for example, taking 11 seconds to train the statistical classifier, and 2 minutes to apply the trained statistical classifier for detection of architectural distortion in un-optimized Matlab code run on a standard laptop with Intel Core i7 (2.7 GHz) and 16G RAM.

The systems and/or methods were evaluated using publicly available data sets obtained from the MIAS (Mammogram Image Analysis Society) that includes 19 images tagged as including architectural distortion and from the DDSM (digital database for screening mammograms) that include 157 images tagged as including architectural distortion. The images suggest scanned screen file mammograms.

Images were preprocessed. Images from the DDSM were decimated to have the same resolution as images in the MIAS data set (200 micrometers). The MIAS images and DDSM image were both used for evaluation of the RoI classification (as described below). The DDSM data set was used for image classification and localization due to the larger images in the data set. An expert radiologist selected 52 images from 42 patients in which there was high certainty for presence of (spiculated) architectural distortion. The selected set was balanced by 84 normal images from 37 patients.

It is noted that the breast density (the prevalence of the fibroglandular tissue in the breast) plays an important role in architectural distortion detection (both computationally and by radiologists). Of the breasts with architectural distortion abnormalities, 2% were fatty, 71% were glandular, and 27% were extremely dense. These highly dense breasts raise a particular challenge and are likely to obscure the architectural distortion finding. Normal mammograms selected from DDSM were 12% fatty, 56% glandular, and 32% extremely dense breasts.

Two types of tests were conducted to evaluate the systems and/or methods described herein. The first test type is a RoI classification scheme, and an image classification method, that discriminates between images with architectural distortion findings and normal cases (without architectural distortion abnormality). The second test type is the localization of the predicted RoI examined with respect to the marked annotation (ground truth). The performance assessment was carried out with leave-one-patient out cross-validation, in which all the images from the patient under test are excluded from the training set.

The first test type, RoI classification, is now described. The suggested computed representation is evaluated by measuring the discrimination capability with a linear SVM classifier.

Reference is now made to FIG. 7, which is a table 700 depicting performance of the RoI classification performance of the systems and/or methods described herein based on the computed representations determined based on deep neural network transfer learning, in accordance with some embodiments of the present invention. The results are compared to a previous work of Biswas et al. described in detail in Biswas, S. K., Mukherjee, D. P.: Recognizing architectural distortion in mammogram: A multiscale texture modeling approach with GMM. IEEE Trans. Biomed. Eng. 58(7), 2023-2030 (2011), incorporated herein by reference in it's entirely. The method of Biswas et al., is based on hand crafted features (multi-scale texture modeling). To allow comparison, a similar data set is used, including a subset of images from MIAS and DDSM. The MIAS dataset included 63 RoIs, of which 18 were tagged as architectural distortion and 45 were tagged as normal, while the DDSM test bed included 100 RoIs of which 50 were tagged as including architectural distortion and 50 were tagged as normal.

Significant improvement is achieved by the systems and/or methods described herein (i.e. inventors) over the hand crafted features based method described by Biswas et al. The results show that the architectural distortion methods of the systems and/or methods described herein provide an AUC of 0.90 for MIAS and 0.95 for DDSM datasets. Classification error rates were decreased in MIAS and DDSM by 14% and 18% respectively in comparison to the hand crafted features based method described by Biswas et al.

The second type test, image classification and architectural distortion localization, is now described. The set up includes 480 randomly sampled points in the fibroglandular tissue region (320 points in the interior and 160 points on the boundary). At each point, RoIs are extracted at 3 different scales, 1, 1.2, and 1.4, with the nominal scale set as 128×128 bounding box (approximately 25×25 millimeters (mm)). Clusters with less than 15 members were removed.

To validate the image classification (as described herein), the DDSM cohort including cases of architectural distortion (defined as positive) and a set of normal images (defined as negative) is used. A trained binary classifier (mathematically represented as C: I→y∈{−1,1}) is applied to divide the data set into architectural distortion containing and normal images.

Figure 8:
FIG. 8 is a table depicting classification performance of the classifier, and localization accuracy for two variants of the systems and/or methods described herein, as well as comparison to previous methods in accordance with some embodiments of the present invention.

Reference is now made to FIG. 8, which is a table 800 depicting classification and localization accuracy based on the systems and/or methods described herein (i.e., DS-RCNN) at two sensitivity work points, in accordance with some embodiments of the present invention. BR×4 denotes results for a ×4 sampling from the entire breast (as described herein in additional detail). Results for faster R-CNN with learned object proposal and several methods based on published works are shown (as described below in additional detail). $FP_D$ and $FP_T$ denote two measures for average false-positives defined in equations (3) and (4) below.

It is noted that for the image classification task, the DS-RCNN (based on the systems and/or methods described herein) provides the best result with nearly 80% sensitivity and specificity rages. In terms of localization accuracy, DS-RCNN achieves 0.83 detection rate at $FP_T$=0.46 false positives per image (FFPI). The faster R-CNN gains a low specificity in the image classification task and object localization accuracy. The reason is most likely assumed to be due to insufficient samples for the region proposal to suggest relevant regions and for the end to end training or fine tuning of the network.

It is noted that since the search is performed in the fibroglandular tissue domain, a 2% miss is reflected in the performance due to imperfection of the fibroglandular segmentation process.

A symmetric overlap ratio measure is presented. The symmetric overlap ratio may be used to validate the localization of architectural distortion. t denotes the annotation set. $p_i$ denotes the predicted RoI that includes the architectural distortion. The symmetric overlap ratio is denoted as:

$$\mathcal{R}_i = \mathcal{R}(p_i) = \max\left(\frac{|t \cap p_i|}{|t|}, \frac{|t \cap p_i|}{|p_i|}\right), \quad \text{[equation 2]}$$

$$\text{s.t. } m \le |p_i| \le M$$

where the predicted RoI (that includes the architectural distortion) is bounded by the lowest and highest scale factor denoted as [m,M]. The predicted mask is obtained as the union of RoIs that overlap the true mask over a certain ratio, mathematically represented as:

$$p_k = \bigcup_i \{p_i \mid \mathcal{R}_i \ge \alpha\},$$

where:
  i indexes the RoI and k indexes the image.
  α denotes a threshold on the overlap ratio (set as 0.4 in the evaluation calculations described below, denoting 40% overlap)
  The true positive and false positive measures for localization are defined as:

$$TPR = \frac{\#\{\mathcal{R}(p_k) \ge \alpha\}}{\#\{AD \text{ findings in the images classified as true}\}} \quad \text{[equation 3]}$$

$$FPI_D = \frac{\#\{\mathcal{R}_i < \alpha\}}{\#\{\text{images classified as true}\}} \quad \text{[equation 4]}$$

$$FPI_T = \frac{\#\{\mathcal{R}_i < \alpha\}}{\#\{\text{images in the cohort}\}} \quad \text{[equation 5]}$$

where two false positive measures are defined for localization, $FPI_D$ as the FPs per image in the images classified as positive (including architectural distortion) and $FPI_T$ denoting FPs per image in the total cohort.

Table 800 depicts results comparing the systems and/or methods described herein for two sensitivity work points compared with a variation of the systems and/or methods described herein (denoted BR×4) where the whole breast interior is considered for training and testing, rather than the segmented fibroglandular tissue region. Note that in the BR×4 scenario, a 4 times higher sampling rate was used to reach a similar sensitivity to that of sampling the segmented fibroglandular tissue region. Training a classifier using a large number of irrelevant samples reduces computational efficiency and yields a weaker classifier. For comparison, table 800 includes results based on previous works by others, including Rangayyan described with reference to Rangayyan, R. M., Banik, S., Chakraborty, J., Mukhopadhyay, S., Desautels, J. E. L.: Measures of divergence of oriented patterns for the detection of architectural distortion in prior mammograms. Int. J. Comput. Assist. Radiol. Surg. 8(4), 527-545 (2013), Matsubara described with reference to Matsubara, T., Ito, A., Tsunomori, A., Hara, T., Muramatsu, C., Endo, T., Fujita, H.: An automated method for detecting architectural distortions on mammograms using direction analysis of linear structures. EMBC pp. 2661{2664 (2015), and Yoshikawa described with reference to Yoshikawa, R., Teramoto, A., Matsubara, T., Fujita, H.: Automated detection of architectural distortion using improved adaptive gabor filter. In: Proc. Of IWDM2014 (2014), all of which are incorporated herein by reference in their entirety. The best results appear to be reported by Yoshikawa et al. with 1.0 FPs/image @ 0.83 TPR. It is noted that although the performance indexes quoted in table 800 by others provide a subjective evaluation due to different data sets/experimental setup, the results obtained by the systems and/or methods described herein present a significant improvement in reducing the false positive per image by 42% in comparison to the best results in the literature known to the inventors. Note that error rate of below 1 FPs/image is obtained for the first time at about 80% sensitivity.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant mammograms will be developed and the scope of the term mammogram is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for using a trained statistical classifier for detecting an indication of architectural distortion in a mammographic image, comprising:

receiving a two dimensional (2D) mammographic image of a breast;

segmenting fibroglandular tissue of the breast to create a segmented fibroglandular tissue region;

extracting a plurality of regions within the segmented fibroglandular tissue region and within a boundary portion between the segmented fibroglandular tissue and non-fibroglandular tissue;

computing representations for each region of interest (RoI) by a pre-trained deep neural network;

training a classifier on the computed representations to compute a respective probability score of architectural distortion associated with each RoI;

defining each RoI having the probability score above a threshold as positive for architectural distortion;

clustering the RoIs defined as positive using a mean-shift method and providing an indication of the probability of the presence of architectural distortion around a cluster based on a probability distribution of cluster RoI members;

removing small clusters created by the clustering of the RoI according to a small number threshold, wherein clusters having fewer RoI members than the small number threshold are removed;

classifying the image as positive for the indication of architectural distortion when at least one cluster remains after the removing, or classifying the image as negative for the indication of architectural distortion when no cluster remains after the removing; and outputting a classification of the image.

2. The method of claim 1, further comprising when the image is classified as positive, applying a regression operation to the RoIs to obtain at least one localization and prediction for the RoI size indicative of the region within the 2D mammographic image where the architectural distortion is identified.

3. The method of claim 1, further comprising, when the image is classified as positive, applying a secondary meanshift clustering method to the RoIs having probability scores above a second threshold, to select at least one localization RoI indicative of localization of the indication of the architectural distortion within the 2D mammographic image.

4. The method of claim 3, further comprising, marking on the 2D mammographic image, the location of the indication of the architectural distortion corresponding to the location of the at least one localization RoI.

5. The method of claim 3, further comprising computing a union of a plurality of the localization RoIs, the union indicative of the indication of the architectural distortion.

6. The method of claim 1, wherein the fibroglandular tissue is segmented by applying an unsharp mask filter to the mammographic image to obtain a first processed image, normalizing the values of the pixels of the first processed image, and applying threshold to the normalized values to obtain the segmented fibroglandular tissue.

7. The method of claim 1, wherein the RoIs are extracted by sparse and random sampling of the segmented fibroglandular tissue.

8. The method of claim 1, wherein negative RoIs are defined entirely within the segmented fibroglandular tissue.

9. The method of claim 1, wherein the mean shift method used for clustering the RoIs defined as positive is a nonparametric clustering technique that does not require prior knowledge of the number of clusters.

10. The method of claim 1, wherein the neural network is implemented as a deep neural network.

11. The method of claim 1, wherein the classifier is trained using deep neural network transfer learning that is based on using intermediate outputs of a pretrained neural network obtained from at least one lower layer.

12. The method of claim 1, wherein the classifier is implemented as a cascade classifier implemented as a linear support vector machine (SVM).

13. The method of claim 1, further comprising computing a symmetric overlap ratio used to validate the localization of architectural distortion, the symmetric overlap ratio denoted as:

$$\mathcal{R}_i = \mathcal{R}(p_i) = \max\left(\frac{|t \cap p_i|}{|t|}, \frac{|t \cap p_i|}{|p_i|}\right), \text{ s.t. } m \leq |p_i| \leq M$$

wherein:
t denotes an annotation set,
$p_i$ denotes the predicted RoI that includes the architectural distortion, m, and M denote respectively the bounding lowest and highest scale factors that bound the RoI that includes the architectural distortion, wherein the predicted mask is obtained as the union of RoIs that overlap the true mask over a certain ratio denoted as:

$$p_k = \bigcup_i \{p_i \mid \mathcal{R}_i \geq \alpha\},$$

wherein:
i denotes the index of the RoI,
k denotes the indexes of the image,
α denotes a threshold on the overlap ratio,
wherein true positive and false positive measures for localization are defined as:

$$TPR = \frac{\#\{\mathcal{R}(p_k) \geq \alpha\}}{\#\{AD \text{ findings in the images classified as true}\}}.$$

14. A method for training a statistical classifier for detecting an indication of architectural distortion in a mammographic image of a breast, comprising:

receiving a set of training 2D mammographic member images including a sub-set of 2D mammographic images labeled as positive for architectural distortion, wherein the 2D mammographic images comprise screening mammographic images, wherein a size of the sub-set being inadequate for training a standard R-CNN to achieve statistically significant classification;

segmenting fibroglandular tissue of the breast of each member image to create a segmented fibroglandular tissue region;

extracting positive RoIs from regions around an identified architectural distortion of the sub-set of 2D mammographic images labeled as positive for architectural distortion;

extracting negative RoIs from random regions in the fibroglandular tissues of normal mammographic images that are not labeled as positive for architectural distortion; computing representations for each RoI using a pre-trained neural network;

training a binary object cascade classifier, using the computed representations, to compute a respective probability score indicative of architectural distortion associated with each RoI; and providing the trained binary object cascade classifier for classifying a new 2D mammographic image as positive for the indication of architectural distortion.

15. The method of claim 14, further comprising apply image augmentation to the positive RoIs.

16. The method of claim 14, wherein the size of the subset is less than 100 2D mammographic images labeled as positive for architectural distortion.

17. The method of claim 14, further comprising training a regressor to localize the architectural distortion, based on the RoIs classified as including architectural distortion by the classifier based on a high probability score above a threshold, wherein the RoIs classified as including architectural distortion overlap an annotated region defined as including the architectural distortion.

18. The method of claim 14, wherein the binary object cascade classifier is trained by returning samples incorrectly rejected at a first cascade level as input into a following cascade level.

19. The method of claim 14, wherein the training images labeled as positive for architectural distortion are annotated with a simple marking such as bounding box, defining a boundary of an annotated region containing the architectural distortion.

20. A system for using a trained statistical classifier for detecting an indication of architectural distortion in a mammographic image, comprising:
 a program store storing code; and
 a processor coupled to the program store for implementing the stored code, the code comprising:
  code to receive a two dimensional (2D) mammographic image of a breast;
  code to segment fibroglandular tissue of the breast to create a segmented fibroglandular tissue region, extract a plurality of regions within the segmented fibroglandular tissue region and within a boundary portion between the segmented fibroglandular tissue and non-fibroglandular tissue, compute representations for each RoI by a neural network trained on a plurality of sample 2D mammographic images using automatically identified and extracted features, apply a classifier to the computed representations to compute a respective probability score of architectural distortion associated with each RoI, define each RoI having the probability score above a threshold as positive for architectural distortion, cluster the RoIs defined as positive using a mean-shift method to provide an indication of the probability of the presence of architectural distortion for each respective RoI, remove small clusters created by the clustering of the RoI according to a small number threshold, wherein clusters having fewer RoI members than the small number threshold are removed, classify the image as positive for the indication of architectural distortion when at least one cluster remains after the removing, or classify the image as negative for the indication of architectural distortion when no cluster remains after the removing; and
 output a classification of the image.

* * * * *